United States Patent [19]

Müller-Gliemann et al.

[11] Patent Number: 6,121,330
[45] Date of Patent: Sep. 19, 2000

[54] 5-HYDROXYALKYL SUBSTITUTED PHENYLS AND THEIR USE IN MEDICAMENTS FOR THE TREATMENT OF ARTERIOSCLEROSIS AND HYPERLIPOPROTEINAEMIA

[75] Inventors: Matthias Müller-Gliemann, Solingen; Rolf Angerbauer, Wuppertal; Arndt Brandes, Wuppertal; Michael Lögers, Wuppertal; Carsten Schmeck, Wuppertal; Gunter Schmidt, Wuppertal; Klaus-Dieter Bremm, Recklinghausen; Hilmar Bischoff; Delf Schmidt, both of Wuppertal, all of Germany

[73] Assignee: Bayer Aktiengesellschaft, Leverkusen, Germany

[21] Appl. No.: 09/341,983

[22] PCT Filed: Jan. 23, 1998

[86] PCT No.: PCT/EP98/00361

§ 371 Date: Sep. 2, 1999

§ 102(e) Date: Sep. 2, 1999

[87] PCT Pub. No.: WO98/34895

PCT Pub. Date: Aug. 13, 1998

[30] Foreign Application Priority Data

Feb. 5, 1997 [DE] Germany .................. 197 04 244

[51] Int. Cl.⁷ .................. A61K 31/045; A61K 31/12; C07C 33/34; C07C 41/00; C07C 49/76
[52] U.S. Cl. .................. 514/730; 514/717; 514/679; 514/684; 568/807; 568/659; 568/661; 568/332
[58] Field of Search .................. 568/807, 659, 568/661, 332; 514/730, 717, 679, 684

[56] References Cited

U.S. PATENT DOCUMENTS

| | | |
|---|---|---|
| 5,006,530 | 4/1991 | Angerbauer et al. . |
| 5,169,857 | 12/1992 | Angerbauer et al. . |
| 5,401,746 | 3/1995 | Angerbauer et al. . |
| 5,494,605 | 2/1996 | Kurihara et al. .................. 252/299.66 |
| 5,739,166 | 4/1998 | Reitz et al. .................. 514/602 |

FOREIGN PATENT DOCUMENTS 0 325 130   7/1989   European Pat. Off. .

OTHER PUBLICATIONS

J. Org. Chem. (1979), 44(26), 4749–52.
Dinchuk, et al., BBA 1255 (1995) 301–310.

*Primary Examiner*—Deborah C. Lambkin
*Attorney, Agent, or Firm*—Norris, McLaughlin & Marcus, P.A.

[57] ABSTRACT

The novel 5-hydroxy-alkyl-substituted phenyls are prepared by either reacting the corresponding benzaldehydes with the Grignard compounds and subsequently reducing the other functional groups or by reducing the corresponding benzoic esters by customary methods to give the corresponding hydroxyl compounds. The 5-hydroxy-alkyl-substituted phenyls are suitable for use as active compounds in medicaments, in particular for the treatment of dyslipidaemia.

7 Claims, No Drawings

5-HYDROXYALKYL SUBSTITUTED PHENYLS AND THEIR USE IN MEDICAMENTS FOR THE TREATMENT OF ARTERIOSCLEROSIS AND HYPERLIPOPROTEINAEMIA

This application is a 371 of PCT/EP93/00361 Oct. 23, 1998.

The present invention relates to 5-hydroxy-alkyl-substituted phenyls, to processes for their preparation and to their use in medicaments.

The publication U.S. Pat. No. 5,169,857 A2 discloses 7-(polysubstituted pyridyl)-6-heptenoates for the treatment of arteriosclerosis, lipoproteinaemia and hyperlipoproteinaemia. Moreover, the preparation of 7-(4-aryl-3-pyridyl)-3,5-dihydroxy-6-heptenoate is described in the publication EP 325 130 A2. Furthermore, polyarylbenzenes are disclosed in the publication J.Org.Chem. (1979), 44(26), 4749–52.

The present invention, accordingly, provides 5-hydroxy-alkyl-substituted phenyls of the general formula (I)

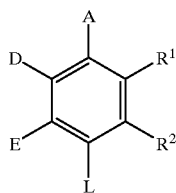

(I)

in which

A represents aryl having 6 to 10 carbon atoms which is optionally substituted up to 5 times by identical or different substituents from the group consisting of halogen, hydroxyl, trifluoromethyl, trifluoromethoxy, nitro, or by straight-chain or branched alkyl, acyl, hydroxyalkyl or alkoxy having in each case up to 7 carbon atoms, or by a group of the formula $-NR^3R^4$ in which $R^3$ and $R^4$ are identical or different and each represents hydrogen, phenyl, or straight-chain or branched alkyl having up to 6 carbon atoms, D represents aryl having 6 to 10 carbon atoms which is optionally substituted by nitro, halogen, trifluoromethyl or trifluoromethoxy, or represents a radical of the formula

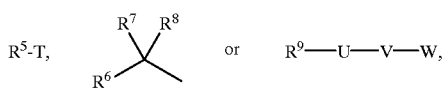

in which $R^5$, $R^6$ and $R^9$ are identical or different and each represents cycloalkyl having 3 to 6 carbon atoms or aryl having 6 to 10 carbon atoms or forms a 5- to 7-membered, optionally benzo-fused, saturated or unsaturated, mono-, bi- or tricyclic heterocycle having up to 4 carbon atoms from the group consisting of S, N and O, where the cycles, in the case of the nitrogen-containing rings also via the N-function, are optionally substituted up to 5 times by identical or different substituents from the group consisting of halogen, trifluoromethyl, nitro, hydroxyl, cyano, carboxyl, trifluoromethoxy, straight-chain or branched acyl, alkyl, alkylthio, alkylalkoxy, alkoxy and alkoxycarbonyl having in each case up to 6 carbon atoms, by aryl having 6 to 10 carbon atoms or by an optionally benzo-fused aromatic 5- to 7-membered heterocycle having up to 3 heteroatoms from the group consisting of S, N and/or O, and/or by a group of the formula $-OR^{10}$, $-SR^{11}$, $-SO_2R^{12}$ or $-NR^{13}R^{14}$, in which $R^{10}$, $R^{11}$ and $R^{12}$ are identical or different and each represents aryl having 6 to 10 carbon atoms which for its part is substituted up to 2 times by identical or different substituents from the group consisting of phenyl, halogen or by straight-chain or branched alkyl having up to 4 carbon atoms, $R^{13}$ and $R^{14}$ are identical or different and have the meaning of $R^3$ and $R^4$ given above, or $R^5$ or $R^6$ represent a radical of the formula

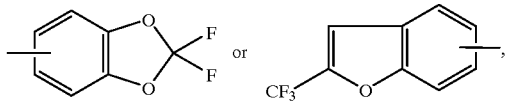

T represents straight-chain or branched alkyl or alkenyl having in each case 2 to 10 carbon atoms which are optionally substituted up to 2 times by hydroxyl, $R^7$ represents hydrogen or halogen, and $R^8$ represents hydrogen, halogen, azido, trifluoromethyl, hydroxyl, trifluoromethoxy, straight-chain or branched alkoxy having up to 5 carbon atoms or a radical of the formula $-NR^{15}R^{16}$, in which $R^{15}$ and $R^{16}$ are identical or different and have the meaning of $R^3$ and $R^4$ given above, or $R^7$ and $R^8$ together form a radical of the formula $=O$ or $=NR^{17}$, in which $R^{17}$ is hydrogen or straight-chain or branched alkyl, alkoxy or acyl having in each case up to 6 carbon atoms, U and W are identical or different and each represents straight-chain or branched alkyl having up to 8 carbon atoms, or U or W represent a bond, V represents an oxygen or sulphur atom or represents a radical of the formula $-NR^{18}$, in which $R^{18}$ represents hydrogen or straight-chain or branched alkyl having up to 6 carbon atoms or phenyl, E represents cycloalkyl having 3 to 8 carbon atoms, or represents straight-chain or branched alkyl having up to 8 carbon atoms which is optionally substituted by cycloalkyl having 3 to 8 carbon atoms or hydroxyl, or represents phenyl which is optionally substituted by halogen or trifluoromethyl, L represents hydrogen, hydroxyl, straight-chain or branched alkoxy or alkyl having in each case up to 6 carbon atoms or represents a radical of the formula $-NR^{19}R^{20}$ or

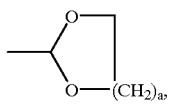

in which $R^{19}$ and $R^{20}$ have the meanings of $R^3$ and $R^4$ given above and are identical to or different from these, and a represents a number 1, 2 or 3, $R^1$ represents straight-chain or branched alkyl having up to 6 carbon atoms which is substituted by hydroxyl, $R^2$ represents aryl having 6 to 10 carbon atoms which is optionally substituted by halogen, nitro, cyano, trifluoromethyl, trifluoromethoxy, straight-chain or branched alkyl, alkoxy, acyl or alkoxycarbonyl having in each case up to 6 carbon atoms, hydroxyl, carboxyl or by a group of the formula —$NR^{21}R^{22}$, in which $R^{21}$ and $R^{22}$ are identical or different and have the meanings of $R^3$ and $R^4$ given above, and their salts.

The 5-hydroxy-alkyl-substituted phenyls according to the invention may also be present in the form of their salts. In general, salts of organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metals or ammonium salts of the compounds according to the invention which have a free carboxyl group. Particular preference is given to, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either behave as image and mirror image (enantiomers), or which do not behave as image and mirror image (diastereomers). The invention relates both to the enantiomers or diastereomers or to their respective mixtures. These mixtures of the enantiomers and diastereomers can be separated into the stereoisomerically uniform constituents in a known manner.

Heterocycle, if appropriate benzo-fused, in the context of the invention in general represents a saturated or unsaturated 5- to 7-membered, preferably 5- to 6-membered, heterocycle, which can contain up to 3 heteroatoms from the group consisting of S, N and O. Examples which may be mentioned are, indolyl, isoquinolyl, quinolyl, benzo[b]thiophene, benzo[b]furanyl, pyridyl, thienyl, furyl, pyrrolyl, thiazolyl, oxazolyl, imidazolyl, morpholinyl or piperidyl. Quinolyl, furyl, pyridyl and thienyl are preferred.

Preferred compounds of the general formula (I) according to the invention are those in which A represents naphthyl or phenyl which are optionally substituted up to 3 times by identical or different substituents from the group consisting of fluorine, chlorine, bromine, amino, hydroxyl, trifluoromethyl, trifluoromethoxy, nitro, or by straight-chain or branched alkyl, or alkoxy having in each case up to 6 carbon atoms or by a group of the formula —$NR^3R^4$, in which $R^3$ and $R^4$ are identical or different and each represents hydrogen or straight-chain or branched alkyl having up to 4 carbon atoms, D represents phenyl which is optionally substituted by nitro, fluorine, chlorine, bromine, phenyl, trifluoromethyl or trifluoromethoxy, or represents a radical of the formula

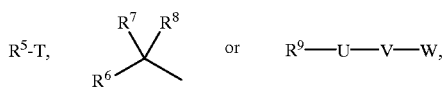

in which $R^5$, $R^6$ and $R^9$ independently of one another each represent cyclopropyl, cyclopentyl or cyclohexyl, or phenyl, naphthyl, pyridyl, tetrazolyl, pyrimidyl, pyrazinyl, pyrrolidinyl, indolyl, morpholinyl, imidazolyl, benzothiazolyl, phenoxathiin-2-yl, benzoxazolyl, furyl, quinolyl or purin-8-yl, where the cycles are optionally substituted up to 3 times, in the case of the nitrogen-containing rings also via the N-function, by identical or different substituents from the group consisting of fluorine, chlorine, bromine, trifluoromethyl, hydroxyl, cyano, carboxyl, trifluoromethoxy, straight-chain or branched acyl, alkyl, alkylthio, alkylalkoxy, alkoxy or alkoxycarbonyl having in each case up to 4 carbon atoms, triazolyl, tetrazolyl, benzoxathiazolyl or phenyl, and/or by a group of the formula —$OR^{10}$, —$SR^{11}$ or —$SO_2R^{12}$, in which $R^{10}$, $R^{11}$ and $R^{12}$ are identical or different and each represents phenyl which for its part is substituted up to 2 times by identical or different substituents from the group consisting of phenyl, fluorine, chlorine or by straight-chain or branched alkyl having up to 4 carbon atoms, or $R^5$ and/or $R^6$ represent a radical of the formula

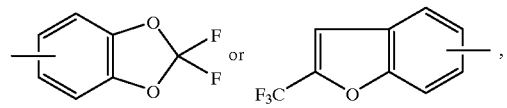

$R^7$ represents hydrogen, fluorine, chlorine or bromine, and $R^8$ represents hydrogen, fluorine, chlorine, bromine, azido, trifluoromethyl, hydroxy, trifluoromethoxy, straight-chain or branched alkoxy or alkyl having in each case up to 5 carbon atoms or a radical of the formula —$NR^{15}R^{16}$, in which $R^{15}$ and $R^{16}$ are identical or different and each represents hydrogen, phenyl or straight-chain or branched alkyl having up to 4 carbon atoms, or $R^7$ and $R^8$ together form a radical of the formula =O or =$NR^{17}$, in which $R^{17}$ represents hydrogen or straight-chain or branched alkyl, alkoxy or acyl having in each case up to 4 carbon atoms, T represents straight-chain or branched alkyl or alkenyl having in each case up to 6 carbon atoms which are optionally substituted up to 2 times by hydroxyl, U and W are identical or different and each represents straight-chain or branched alkylene having up to 6 carbon atoms, or U or W represent a bond, V represents an oxygen or sulphur atom or a group of the formula —$NR^{18}$, in which $R^{18}$ represents hydrogen or straight-chain or branched alkyl having up to 4 carbon atoms or phenyl, E represents cyclopropyl, -butyl, -pentyl, -hexyl or -heptyl, or represents straight-chain or branched alkyl having up to 6 carbon atoms which is optionally substituted by cyclopropyl, -butyl, -hexyl, -pentyl, -heptyl, or by hydroxyl, or represents phenyl which is optionally substituted by fluorine, chlorine or trifluoromethyl, L represents hydrogen, hydroxyl, straight-chain or branched alkoxy or alkyl having in each case up to 5 carbon atoms or represents a radical of the formula —$NR^{19}R^{20}$, in which $R^{19}$ and $R^{20}$ have the meanings of $R^3$ and $R^4$ given above and are identical to or different from these, $R^1$ represents straight-chain or branched alkyl having up to 4 carbon atoms which is substituted by hydroxyl, $R^2$ represents naphthyl or phenyl which is optionally substituted by fluorine, chlorine, bromine, nitro, cyano, trifluoromethyl, trifluoromethoxy, straight-chain or branched alkyl, alkoxy, acyl or alkoxycarbonyl having in each case up to 4 carbon atoms, hydroxyl, carboxyl or by a group of the formula —$NR^{21}R^{22}$, in which $R^{21}$ and $R^{22}$ are identical or different and have the meanings of $R^3$ and $R^4$ given above, and their salts.

Particular preference is given to compounds of the general formula (I) according to the invention in which A represents phenyl which is optionally substituted up to 2 times by identical or different substituents from the group consisting of fluorine, chlorine, bromine, hydroxyl, trifluoromethyl, trifluoromethoxy, nitro, or by straight-chain or branched alkyl or alkoxy having in each case up to 5 carbon atoms or by a group of the formula —$NR^3R^4$, in which $R^3$ and $R^4$ are identical or different and each represents hydrogen or straight-chain or branched alkyl having up to 3 carbon atoms, D represents phenyl which is optionally substituted by nitro, phenyl, fluorine, chlorine or bromine, or represents a radical of the formula

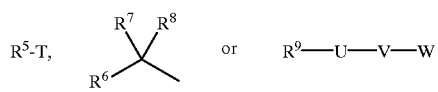

in which $R^5$, $R^6$ and $R^9$ independently of one another each represent cyclopropyl, cyclopentyl or cyclohexyl, or phenyl, naphthyl, pyridyl, tetrazolyl, pyrimidyl, pyrazinyl, phenoxathiin-2-yl, indolyl, imidazolyl, pyrrolidinyl, morpholinyl, benzothiazolyl, benzoxazolyl, furyl, quinolyl or purin-8-yl, where the cycles are optionally substituted up to 3 times, in the case of the nitrogen-containing rings also via the N-function, by identical or different substituents from the group consisting of fluorine, chlorine, trifluoromethyl, hydroxyl, cyano, carboxyl, trifluoromethoxy, straight-chain or branched alkyl, alkylthio, alkylalkoxy, alkoxy or alkoxycarbonyl having in each case up to 3 carbon atoms, triazolyl, tetrazolyl, benzothiazolyl and phenyl, and/or by a group of the formula —$OR^{10}$, —$SR^{11}$ or —$SO_2R^{12}$, in which $R^{10}$, $R^{11}$ and $R^{12}$ are identical or different and each represents phenyl which for its part is substituted up to 2 times by identical or different substituents from the group consisting of phenyl, fluorine, chlorine, or by straight-chain or branched alkyl having up to 3 carbon atoms, or $R^5$ and/or $R^6$ represent a radical of the formula

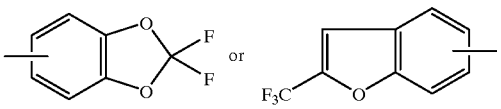

$R^7$ represents hydrogen or fluorine, and $R^8$ represents hydrogen, fluorine, chlorine, bromine, azido, trifluoromethyl, hydroxyl, trifluoromethoxy, or straight-chain or branched alkoxy or alkyl having in each case up to 4 carbon atoms or represents a radical of the formula —$NR^{15}R^{16}$, in which $R^{15}$ and $R^{16}$ are identical or different and each represents hydrogen or straight-chain or branched alkyl having up to 3 carbon atoms, or $R^7$ and $R^8$ together form a radical of the formula =O or =$NR^{17}$, in which $R^{17}$ represents hydrogen or straight-chain or branched alkyl, alkoxy or acyl having in each case up to 4 carbon atoms, T represents straight-chain or branched alkyl or alkenyl having in each case up to 4 carbon atoms which are optionally substituted up to 2 times by hydroxyl, U and W are identical or different and each represents straight-chain or branched alkyl having up to 3 carbon atoms, or U or W represent a bond, V represents an oxygen or sulphur atom or a group of the formula —$NR^{18}$, in which $R^{18}$ represents hydrogen or straight-chain or branched alkyl having up to 3 carbon atoms, E represents cyclopropyl, cyclopentyl or cyclohexyl or phenyl which is optionally substituted by fluorine or trifluoromethyl, or represents straight-chain or branched alkyl having up to 4 carbon atoms which is optionally substituted by hydroxyl, L represents hydrogen, hydroxyl, straight-chain or branched alkoxy or alkyl having in each case up to 4 carbon atoms or represents a radical of the formula —$NR^{19}R^{20}$, in which $R^{19}$ and $R^{20}$ have the meanings of $R^3$ and $R^4$ given above and are identical to or different from these, $R^1$ represents straight-chain or branched alkyl having up to 3 carbon atoms which is substituted by hydroxyl, $R^2$ represents phenyl which is optionally substituted by fluorine, chlorine, nitro, cyano, trifluoromethyl, trifluoromethoxy, straight-chain or branched alkyl, alkoxy, acyl or alkoxycarbonyl having in each case up to 3 carbon atoms, hydroxyl, carboxyl or by a group of the formula —$NR^{21}R^{22}$, in which $R^{21}$ and $R^{22}$ are identical or different and have the meanings of $R^3$ and $R^4$ given above, and their salts.

Moreover, processes for preparing the compounds of the general formula (I) according to the invention have been found which are characterized in that

[A] in the compounds of the general formula (II)

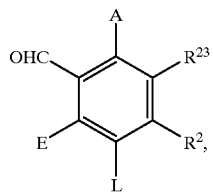
(II)

in which
A, E, L and $R^2$ are each as defined above and
$R^{23}$ represents $C_1$–$C_4$-alkoxycarbonyl,
initially the radical D is generated in the sense of an organometallic reaction, the substituent is optionally derivatized at this stage by customary methods and the alkoxycarbonyl group is converted into the hydroxymethyl function by reduction, or

[B] in the case that D represents the radical of the formula $R^9$—U—V—W in which V represents an oxygen atom, either compounds of the general formula (III)

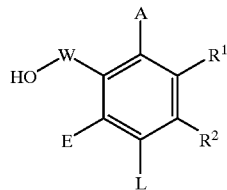
(III)

in which
A, E, L, W, $R^1$ and $R^2$ are each as defined above, are reacted with compounds of the general formula (IV)

 (IV), in which
$R^9$ and U are each as defined above, and
Y represents halogen, preferably chlorine or bromine, in inert solvents, if appropriate in the presence of a base and/or auxiliary, or

[C] compounds of the general formula (III) are initially converted, by reactions with compounds of the general formula (V)

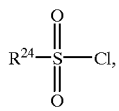
(V)

in which
$R^{24}$ represents straight-chain alkyl having up to 4 carbon atoms, into the compounds of the general formula (VI)

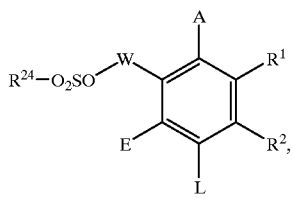
(VI)

in which
A, E, L, W, $R^1$, $R^2$ and $R^{24}$ are each as defined above, and these are subsequently reacted with compounds of the general formula (VII)

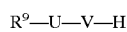 (VII), in which
$R^9$, U and V are each as defined above, and protective groups are, if appropriate, removed, and the substituents listed under D, E, L and/or $R^1$ and $R^2$ are, if appropriate, varied or introduced by customary methods.

The process according to the invention can be illustrated in an exemplary manner by the following schemes:

[A]

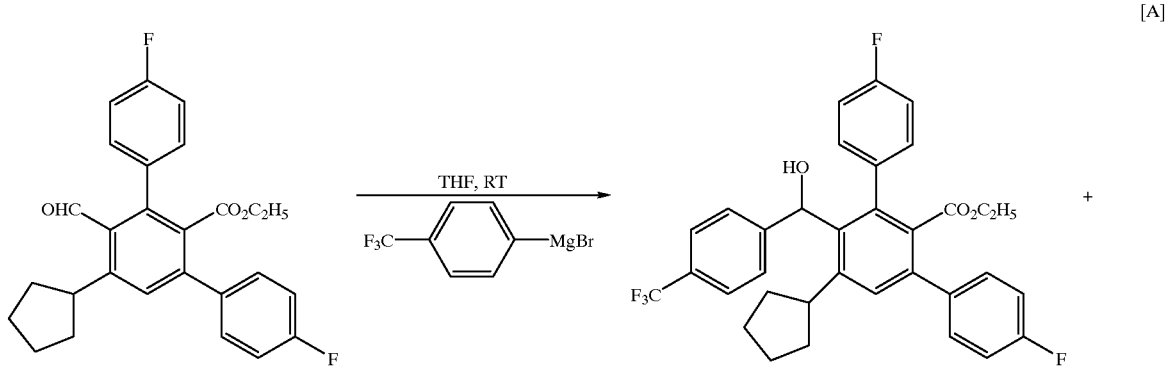

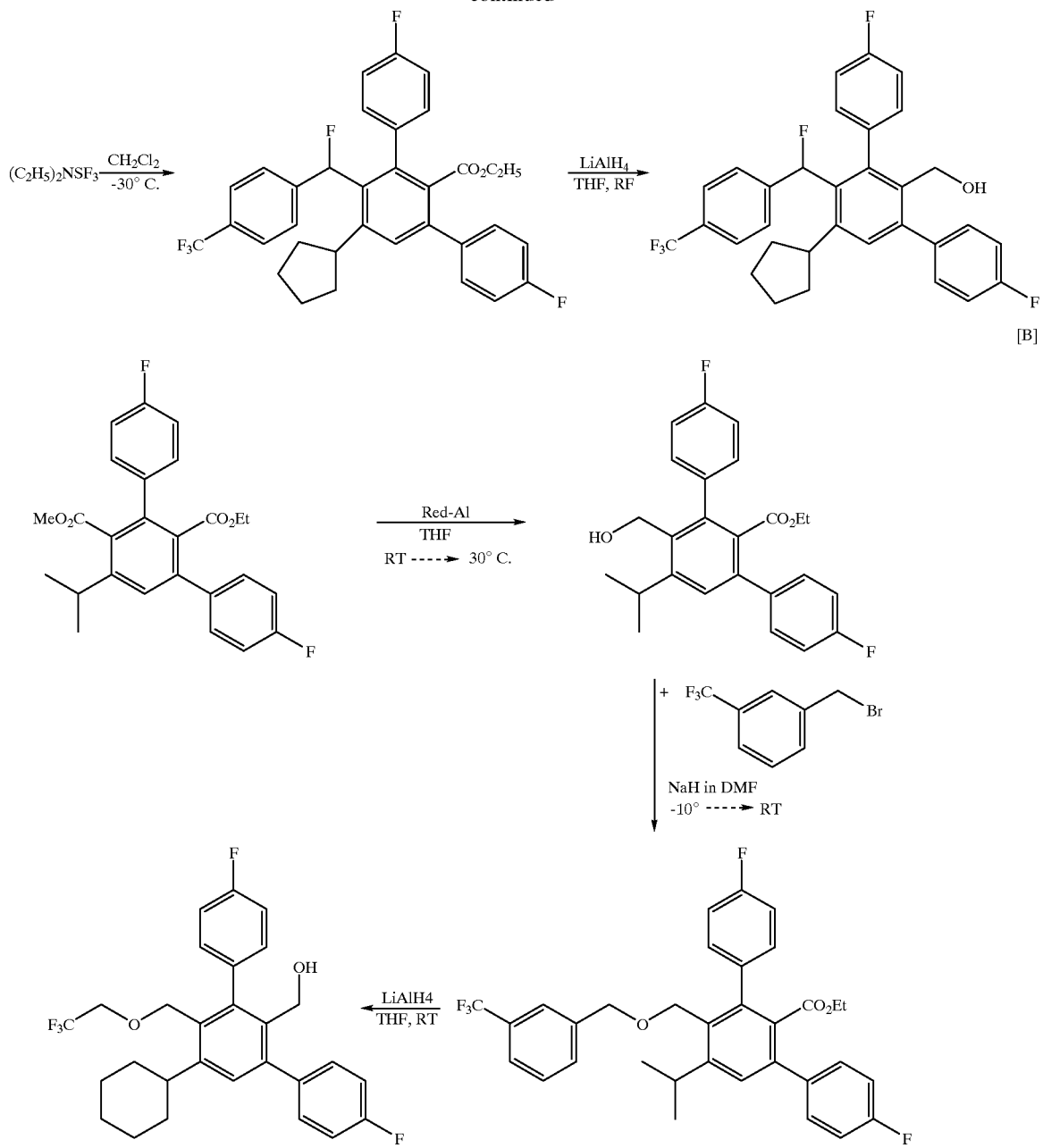

[B]

Suitable solvents for all processes are ethers, such as diethyl ether, dioxane, tetrahydrofuran, glycol dimethyl ether, or hydrocarbons, such as benzene, toluene, xylene, hexane, cyclohexane or petroleum fractions, or halogenohydrocarbons, such as dichloromethane, trichloromethane, carbon tetrachloride, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to use mixtures of the abovementioned solvents. Preference is given to using dichloromethane or toluene.

Bases which are suitable for the individual steps are the customary strongly basic compounds. These preferably include organolithium compounds, such as, for example, N-butyllithium, sec-butyllithium, tert-butyllithium or phenyllithium, or amides, such as, for example, lithium diisopropylamide, sodium amide or potassium amide, or lithium hexamethylsilylamide, or alkali metal hydrides, such as sodium hydride or potassium hydride. Particular preference is given to using N-butyllithium, sodium hydride or lithium diisopropylamide.

Suitable for use in the process [B] are furthermore the customary inorganic bases. These preferably include alkali metal hydroxides or alkaline earth metal hydroxides, such as, for example, sodium hydroxide, potassium hydroxide or barium hydroxide, or alkali metal carbonates, such as sodium carbonate or potassium carbonate, or sodium bicarbonate. Particular preference is given to using sodium hydride or potassium hydroxide.

Suitable organometallic reagents are, for example, systems such as Mg/bromobenzotrifluoride and p-trifluoromethylphenyllithium.

Suitable Wittig reagents are the customary reagents. Preference is given to using 3-trifluoromethylbenzyltriphenylphosphonium bromide.

In general, suitable bases are one of the abovementioned bases, preferably sodium amide.

The base is employed in an amount of from 0.1 mol to 5 mol, preferably from 0.5 mol to 2 mol, in each case based on 1 mol of the starting material.

The reaction with Wittig reagents is generally carried out in a temperature range from 0° C. to 150° C., preferably at from 25° C. to 40° C.

The Wittig reactions are generally carried out at atmospheric pressure. However, it is also possible to carry out the process at reduced pressure or at elevated pressure (for example in the range from 0.5 to 5 bar).

The reductions are generally carried out using reducing agents, preferably those which are suitable for the reduction of ketones to hydroxyl compounds. Particularly suitable in this context is the reduction with metal hydrides or complex metal hydrides in inert solvents, if appropriate in the presence of a trialkylborane. The reduction is preferably carried out using complex metal hydrides such as, for example, lithium borohydride, sodium borohydride, potassium borohydride, zinc borohydride, lithium trialkyl borohydride, diisobutylaluminium hydride or lithium aluminium hydride. Very particular preference is given to carrying out the reduction using diisobutylaluminium hydride and lithium aluminium hydride.

The reducing agent is generally employed in an amount from 1 mol to 6 mol, preferably from 1 mol to 4 mol, based on 1 mol of the compounds to be reduced.

The reduction generally proceeds in a temperature range from −78° C. to +50° C., preferably from −78° C. to 0° C., where, if DIBAH and lithium aluminium hydride are used, the reactions are particularly preferably carried out at from 0° C.—room temperature.

The reduction generally proceeds at atmospheric pressure, but it is also possible to work at elevated or reduced pressure.

The following reaction types may be mentioned as examples of derivatizations: reductions, hydrogenations, halogenations, Wittig/Grignard reactions and amidations.

Bases which are suitable for the individual steps are the customary strongly basic compounds. These preferably include organolithium compounds, such as, for example, N-butyllithium, sec-butyllithium, tert-butyllithium or phenyllithium, or amides, such as, for example, lithium diisopropylamide, sodium amide or potassium amide, or lithium hexamethylsilylamide, or alkali metal hydrides, such as sodium hydride or potassium hydride. Particular preference is given to using N-butyllithium, sodium hydride or lithium diisopropylamide.

Suitable bases are furthermore the customary inorganic bases. These preferably include alkali metal hydroxides or alkaline earth metal hydroxides, such as, for example, sodium hydroxide, potassium hydroxide or barium hydroxide, or alkali metal carbonates, such as sodium carbonate or potassium carbonate, or sodium bicarbonate. Particular preference is given to using sodium hydroxide or potassium hydroxide.

Suitable solvents for the individual reaction steps are also alcohols, such as methanol, ethanol, propanol, butanol or tert-butanol. Preference is given to using tert-butanol.

If appropriate, some reaction steps may have to be carried out under an atmosphere of protective gas.

The halogenations are generally carried out in one of the abovementioned chlorinated hydrocarbons, methylene chloride being preferred.

Suitable halogenating agents are, for example, diethylaminosulphur trifluoride (DAST) or $SOCl_2$.

The halogenation generally proceeds in a temperature range from −78° C. to +50° C., preferably from −78° C. to 0° C., in each case depending on the choice of the halogenating agent and solvent.

The halogenation generally proceeds at atmospheric pressure, but it is also possible to work at elevated or reduced pressure.

Some of the compounds of the general formula (II) are novel, and they can be prepared by converting compounds of the general formula (VIII)

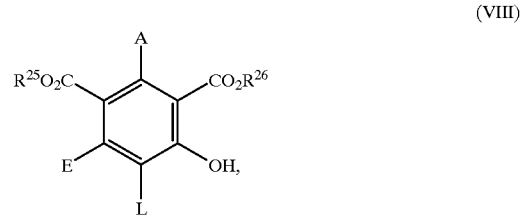

(VIII)

in which

A, E and L are each as defined above, and $R^{25}$ and $R^{26}$ are identical or different and each represent $C_1$–$C_4$-alkyl initially by reaction with $(F_3C—SO_2)_2O$ in pyridine into the compounds of the general formula (IX)

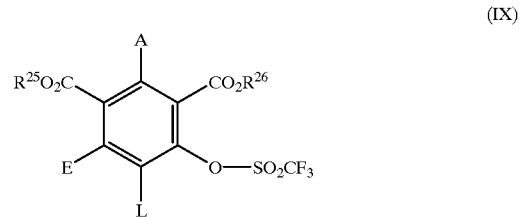

(IX)

in which

A, E, L, $R^{25}$ and $R^{26}$ are each as defined above, subsequently reacting, under exclusion of oxygen, in the system triphenylphosphine, tris-(dibenzylideneacetone)-dipalladium/chloroform complex with compounds of the general formula (X)

$R^1$—Z  (X)

in which $R^1$ is as defined above and

Z represents $B(OH)_2$, to give the compounds of the general formula (XI)

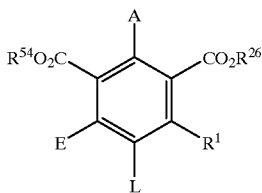

(XI)

in which

A, E, L, $R^1$, $R^{25}$ and $R^{26}$ are each as defined above, reducing, in a further step, the alkoxycarbonyl group ($CO_2R^{25}$) to the hydroxyl function, followed by oxidation to give the formyl group.

Solvents which are suitable for the oxidation are ethers, such as diethyl ether, dioxane, tetrahydrofuran, glycol dimethyl ether, or hydrocarbons, such as benzene, toluene, xylene, hexane, cyclohexane or petroleum fractions, or halogenated hydrocarbons, such as dichloromethane, trichloromethane, carbon tetrachloride, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to use mixtures of the abovementioned solvents. Preference is given to using methylene chloride.

Suitable oxidizing agents are, for example, cerium(IV) ammonium nitrate, thionyl chloride, 2,3-dichloro-5,6-dicyano-benzoquinone, pyridinium chlorochromate (PCC) or pyridinium chlorochromate on basic alumina, osmium tetroxide and manganese dioxide. Preference is given to using thionyl chloride and 2,3-dichloro-5,6-dicyano-benzoquinone.

The oxidizing agent is employed in an amount from 1 mol to 10 mol, preferably from 2 mol to 5 mol, based on 1 mol of the compounds of the general formula (XII).

The oxidation generally proceeds in a temperature range from $-50°$ C. to $+100°$ C., preferably from room temperature to reflux.

The oxidation generally proceeds at atmospheric pressure. However, it is also possible to carry out the oxidation at elevated or reduced pressure.

The compounds of the general formulae (IV), (V), (VI), (VII) and (X) are known per se or can be prepared by customary methods.

Some of the compounds of the general formulae (IX) and (XI) are known, or they are novel, in which case they can be prepared as described above.

Some of the compounds of the general formula (VIII) are known, or they are novel, in which case they can be prepared by known methods.

The compounds of the general formula (I) according to the invention have an unforeseeable spectrum of pharmacological action.

The compounds of the general formula (I) according to the invention have useful pharmacological properties which are superior in comparison with those of the prior art; in particular they are highly effective inhibitors of the cholesterol ester transfer protein (CETP) and stimulate reverse cholesterol transport. The active compounds according to the invention bring about a lowering of the LDL cholesterol level in the blood with a simultaneous increase in the HDL cholesterol level. They can therefore be used for the treatment or prevention of hyperlipoproteinaemia, dyslipidaemiae, hypertriglyceridaemiae or arteriosclerosis.

The pharmacological action of the substances according to the invention were determined in the following test:

CETP Inhibition Testing

Obtainment of CETP

CETP is obtained from human plasma in partially purified form by differential centrifugation and column chromatography and used for the test. To this end, human plasma is adjusted to a density of 1.21 g per ml using NaBr and centrifuged at 4° C. for 18 h at 50,000 rpm. The bottom fraction (d>1.21 g/ml) is applied to a Sephadex®phenyl-sepharose 4B (Pharmacia) column, washed with 0.15 M NaCl/0.001 M trisHCl pH 7.4 and then eluted with distilled water. The CETP-active fractions are pooled, dialyzed against 50 mM Na acetate pH 4.5 and applied to a CM-Sepharose® (Pharmacia) column. The column is then eluted using a linear gradient (0–1 M NaCl). The pooled CETP fractions are dialyzed against 10 mM tris HCl pH 7.4 and then further purified by chromatography on a Mono Q® column (Pharmacia).

Obtainment of Radiolabelled HDL 50 ml of fresh human EDTA plasma is adjusted to a density of 1.12 using NaBr and centrifuged at 50,000 rpm for 18 h at 4° C. in a Ty 65 rotor. The upper phase is used to obtain cold LDL. The lower phase is dialyzed against 3×4 l of PDB buffer (10 mM tris/HCl pH 7.4, 0.15 mM NaCl, 1 mM EDTA, 0.02% $NaN_3$). 20 µl of 3H-cholesterol (Dupont NET-725; 1 µC/µl dissolved in ethanol!) are then added per 10 ml of retentate volume and the mixture is incubated under $N_2$ at 37° C. for 72 h.

The mixture is then adjusted to the density 1.21 using NaBr and centrifuged at 20° C. for 18 h at 50,000 rpm in the Ty 65 rotor. The upper phase is recovered and the lipoprotein fractions are purified by gradient centrifugation. To this end, the isolated, labelled lipoprotein fraction is adjusted to a density of 1.26 using NaBr. Each 4 ml of this solution are covered with a layer of 4 ml of a solution of density 1.21 and 4.5 ml of a solution of 1.063 (density solutions from PDB buffer and NaBr) in centrifuge tubes (SW 40 rotor) and then centrifuged in the SW 40 rotor for 24 h at 38,000 rpm and 20° C. The intermediate layer lying between the densities 1.063 and 1.21 and containing the labelled HDL is dialyzed at 4° C. against 3×100 volumes of PDB buffer. The retentate contains radiolabelled $^3$H-CE-HDL, which is used for the test, adjusted to about $5×10^6$ cmp per ml.

CETP Test

To test the CETP activity, the transfer of $^3$H-cholesterol ester from human HD lipoproteins to biotinylated LD lipoproteins is measured.

The reaction is ended by addition of streptavidin-SPA® beads (Amersham) and the transferred radioactivity is determined directly in a liquid scintillation counter.

In the test mixture, 10 µl of HDL-$^3$H-cholesterol ester (~50,000 cpm) are incubated at 37° C. for 18 h with 10 µl of biotin-LDL (Amersham) in 50 mM Hepes/0.15 M NaCl/0.1% bovine serum albumin/0.05% $NaN_3$ pH 7.4 with 10 µl of CETP (1 mg/ml) and 3 µl of solution of the substance to be tested dissolved (in 10% DMSO/1% RSA). 200 µl of the SPA-streptavidin bead solution (TRKQ 7005) are then added, the mixture is incubated further for 1 h with shaking and then measured in the scintillation counter. As controls, corresponding incubations with 10 µl of buffer, 10 µl of CETP at 4° C. and 10 µl of CETP at 37° C. are used.

The activity transferred into the control mixture with CETP at 37° C. is rated as 100% transfer. The substance concentration at which this transfer is reduced by half is indicated as the $IC_{50}$ value.

In Table A which follows, the $IC_{50}$ values (mol/l) are indicated for CETP inhibitors:

TABLE A

| Example No. | IC$_{50}$ value (mol/l) |
|---|---|
| 1 | $9 \times 10^{-8}$ |
| 3 | $1 \times 10^{-7}$ |
| 4 | $4 \times 10^{-6}$ |

Ex Vivo Activity of the Compounds According to the Invention

Syrian golden hamsters from in-house breeding are anaesthetized after fasting for 24 hours (0.8 mg/kg of atropine, 0.8 mg/kg of Ketavet® s.c., 30' later 50 mg/kg of Nembutal i.p.). The jugular vein is then exposed and cannulated. The test substance is dissolved in a suitable solvent (as a rule Adalat placebo solution: 60 g of glycerol, 100 ml of H$_2$O, PEG-400 to 1000 ml) and administered to the animals via a PE catheter inserted in the jugular vein. The control animals receive the same volume of solvent without test substance. The vein is then tied off and the wound is closed.

The administration of the test substances can also be carried out p.o., by orally administering the substances dissolved in DMSO and suspended in 0.5% Tylose by means of a stomach tube. The control animals receive identical volumes of solvent without test substance.

After various times—up to 24 hours after administration—blood (about 250 µl) is taken from the animals by puncture of the retroorbital venous plexus. Clotting is ended by incubating at 4° C. overnight, then centrifugation is carried out at 6000×g for 10 minutes. In the serum thus obtained, CETP activity is determined by the modified CETP test. As for the CETP test described above, the transfer of $^3$H-cholesterol ester from HD lipoproteins to biotinylated LD lipoproteins is measured.

The reaction is ended by addition of Streptavidin-SPA® beads (Amersham) and the transferred radioactivity is determined directly in the liquid scintillation counter.

The test mixture is carried out as described under "CETP test". For the testing of the serum, only 10 µl of CETP are replaced by 10 µl of the corresponding serum samples. As controls, corresponding incubations with sera of untreated animals are used.

The activity transferred into the control mixture with control sera is rated as 100% transfer. The substance concentration at which this transfer is reduced by half is indicated as the ED$_{50}$ value.

In Vivo Activity of the Compounds According to the Invention

In experiments to determine the oral action on lipoproteins and triglycerides, test substance dissolved in DMSO and 0.5% Tylose suspended by means of a stomach tube are administered orally to Syrian golder hamsters from in-house breeding. To determine the CETP activity, blood (about 250 µl) is taken by retroorbital puncture before the start of the experiment. The test substances are then administered orally by means of a stomach tube. The control animals receive identical volumes of solvent without test substance. The feed is then withdrawn from the animals and blood is taken at various times—up to 24 hours after substance administration—by puncture of the retroorbital venous plexus.

Clotting is ended by incubation at 4° C. overnight, then centrifugation at 6000×g is carried out for 10 minutes. In the serum thus obtained, the content of cholesterol and triglycerides is determined with the aid of modified commercially available enzyme tests (cholesterol enzymatic 14366 Merck, triglycerides 14364 Merck). Serum is suitably diluted using physiological saline solution.

100 µl of serum dilution are mixed with 100 µl of test substance in 96-hole plates and incubated at room temperature for 10 minutes. The optical density is then determined at a wavelength of 492 nM using an automatic plate-reading apparatus. The triglyceride or cholesterol concentration contained in the samples is determined with the aid of a standard curve measured in parallel.

The determination of the content of HDL cholesterol is carried out according to the manufacturer's instructions after precipitation of the ApoB-containing lipoproteins by means of a reagent mixture (Sigma 352-4 HDL cholesterol reagent).

TABLE C

| | HDL rise in in vivo experiments | |
|---|---|---|
| Ex. No. | Dose [mg/kg/d] | % HDL rise |
| 3 | 2 × 30 | 21 |

In Vivo Activity in Transgenic hCETP Mice

Transgenic mice from in-house breeding (Dinchuck, Hart, Gonzalez, Karmann, Schmidt, Wirak; BBA (1995), 1255, 301) were administered the substances to be tested in the feed. Before the start of the experiment, blood was taken retro-orbitally from the mice in order to determine cholesterol and triglycerides in the serum. The serum was obtained as described above for hamsters by incubation at 4° C. overnight and subsequent centrifugation at 6000×g. After one week, blood was again taken from the mice in order to determine lipoproteins and triglycerides. The change in the parameters measured are expressed as a percentage change compared with the starting value.

The invention additionally relates to the combination of substances of the general formula (I) with a glucosidase and/or amylase inhibitor for the treatment of familial hyperlipidaemias, of obesity (adiposity) and of diabetes mellitus. Glucosidase and/or amylase inhibitors in the context of the invention are, for example, acarbose, adiposine, voglibose, miglitol, emiglitate, MDL-25637, camiglibose (MDL-73945), tendamistate, AI-3688, trestatin, pradimicin-Q and salbostatin.

The combination of acarbose, miglitol, emiglitate or voglibose with one of the abovementioned compounds of the general formula (I) according to the invention is preferred.

Furthermore, the compounds according to the invention can be combined in combination with cholesterol-lowering vastatins or Apo B-lowering principles to treat dyslipidaemiae, combined hyperlipidaemiae, hypercholesterolaemiae or hypertriglyceridaemiae.

The combinations mentioned can also be used for primary or secondary prevention of coronary heart diseases (for example myocardiac infarction).

Vastatins in the context of the invention are, for example, lovastatin, simvastatin, pravastatin, fluvastatin, atorvastatin and cerivastatin. Apo B-lowering agents are, for example, MTP inhibitors.

Preference is given to the combination of cerivastatin or Apo B inhibitors with one of the abovementioned compounds of the general formula (I) according to the invention.

The novel active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of approximately 0.5 to 90% by weight of the total mixture, i.e. in amounts which are adequate in order to achieve the dosage range indicated.

The formulations are prepared, for example, by extending the active compounds with solvents and/or excipients, if appropriate using emulsifiers and/or dispersants, it being possible, for example, when water is used as a diluent, optionally to use organic solvents as auxiliary solvents.

Administration is carried out in a customary manner, intravenously, parenterally, perlingually or orally, preferably orally.

In the case of parenteral administration, solutions of the active compound can be employed using suitable liquid excipient materials.

In general, it has proved advantageous in the case of intravenous administration to administer amounts of approximately 0.001 to 1 mg/kg, preferably of approximately 0.01 to 0.5 mg/kg of body weight to achieve effective results, and in the case of oral administration the dosage is approximately 0.01 to 20 mg/kg, preferably 0.1 to 10 mg/kg of body weight.

In spite of this, if appropriate it may be necessary to deviate fom the amounts mentioned, mainly depending on the body weight or the type of administration route, on individual behaviour towards the medicament, the manner of its formulation and the time or interval at which administration takes place. Thus in some cases it may be sufficient to manage with less than the abovementioned minimum amount, while in other cases the upper limit mentioned has to be exceeded. In the case of the administration of relatively large amounts, it may be advisable to divide these into several individual doses over the course of the day.

| Abbreviations used: | | |
|---|---|---|
| C | = | cyclohexane |
| EA | = | ethyl acetate |
| PE | = | petroleum ether |
| THF | = | tetrahydrofuran |
| DAST | = | dimethylaminosulphur trifluoride |
| PTA | = | para-toluenesulphonic acid |
| PDC | = | pyridinium dichromate |
| PE/EA | = | petroleum ether/ethyl acetate |
| DDQ | = | 2,3-dichloro-5,6-dicyano-benzoquinone |
| HCl | = | hydrochloric acid |
| PCC | = | pyridinium chlorochromate |

Starting Materials

EXAMPLE I

2-Methyl 3-ethyl 1-cyclopentyl-3-(4-fluorophenyl)-5-oxo-1-cyclohexene-2,3-dicarboxylate

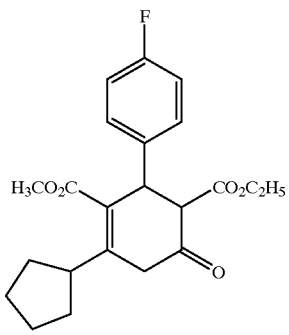

20 g (72.4 mmol) of methyl 1-cyclopentyl-3-(4-fluorophenyl)-1-oxo-2-propene-2-carboxylate and 12.4 g (72.4 mmol) of ethyl 2-(N-isopropyl)-2-propene-carboxylate in 150 ml of ethanol are refluxed overnight. 50 ml of half-concentrated hydrochloric acid are stirred into the cooled solution, and the mixture is refluxed for 17 h.

The cooled solution is partitioned between $CH_2Cl_2$ and water, the aqueous phase is reextracted with $CH_2Cl_2$ and the combined organic phases are dried over $Na_2SO_4$, filtered and concentrated. The crude product is chromatographed over 1 kg of silica gel using EA:PE 1:6.

Yield: 8.4 g (29.8% of theory)

$R_f$=0.73 tol:EA 5:1

EXAMPLE II

3-Methyl 5-ethyl 2-cyclopentyl-4-(4-fluorophenyl)-6-hydroxy-phenyl-3,5-dicarboxylate

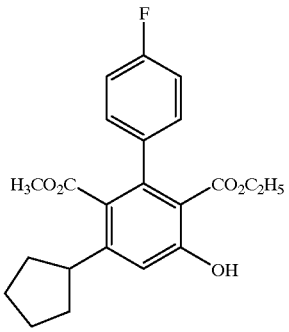

7.3 g (18.8 mol) of the compound from Example I are dissolved in 100 ml of $SOCl_2$ and refluxed for 18 h. The solution is cooled to room temperature and then poured into ice-water, the mixture is diluted with ethyl acetate and extracted, and the organic phase is stirred with $NaHCO_3$ solution and then dried using $Na_2SO_4$, filtered and concentrated. 9 g of crude product are chromatographed over 1 kg of silica gel using PE:EA 4:1.

Yield: 1.12 g (15.4% of theory)

$R_f$=0.74 PE:EA 4:1

EXAMPLE III

3-Methyl 5-ethyl 2-cyclopentyl-4-(4-fluorophenyl)-6-trifluoromethanesulphonylphenyl-3,5-dicarboxylate

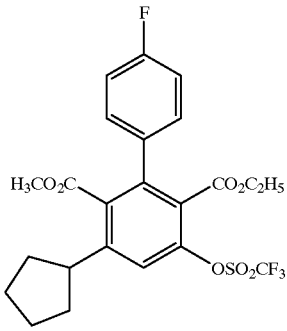

Under argon and at 0° C., 1.55 g (5.6 mmol) of trifluoromethanesulphonic anhydride are added dropwise to a solution of 1.2 g (3.1 mmol) of the compound from Example II in 4 ml of pyridine. The mixture is stirred at room temperature for 18 h and then poured into ice-water and extracted 3 times with ethyl acetate. The combined organic phases are extracted with 10% strength HCl solution, dried over $Na_2SO_4$, filtered and concentrated. The crude product is chromatographed over 150 g of silica gel using toluene.

Yield: 1.04 g (65% of theory)

$R_f$=0.5 toluene

EXAMPLE IV

3-Methyl 5-ethyl 2-cyclopentyl-4-(4-fluorophenyl)-6-(fluorophenyl)phenyl-3,5-dicarboxylate

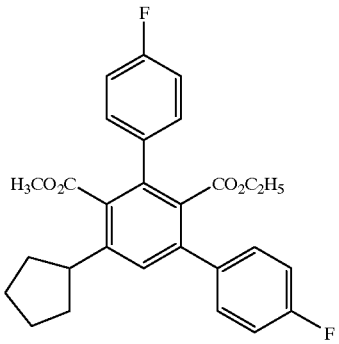

Under strict exclusion of the atmosphere, a solution of 54 mg (0.05 mmol) of tri(dibenzylideneacetone)dipalladium/chloroform complex and 110 mg of triphenylphosphine dissolved in 40 ml of toluene is, after 15 minutes, admixed dropwise with a solution of 1.08 g (2.1 mmol) of the compound from Example III in 40 ml of toluene, then dropwise with a solution of 292 mg (2.1 mmol) of p-fluorophenylboronic acid in 25 ml of methanol and finally dropwise with a solution of 221 mg (2.1 mmol) of $Na_2CO_3$ in 20 ml of $H_2O$. The mixture is refluxed for 18 h. For work-up, the mixture is partitioned between ethyl acetate and $H_2O$ and the organic phase is extracted with saturated NaCl solution, dried over $Na_2SO_4$, filtered and concentrated. The crude product is chromatographed over 300 g of silica gel using toluene.

Yield: 577 mg (59% of theory)

$R_f$=0.47 in toluene

EXAMPLE V

Ethyl 2-cyclopentyl-4,6-bis-(4-fluorophenyl)-3-hydroxymethyl-5-carboxylate

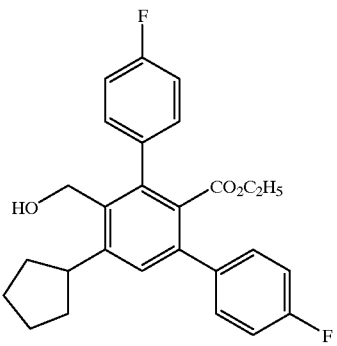

At room temperature and under argon, 1.8 ml of a Red-Al solution (12 mmol) are added dropwise to a solution of 927 mg (2 mmol) of the compound from Example IV in 30 ml of toluene. After 14 h at 40° C., the mixture is hydrolyzed using 20 ml of a saturated Na,K tartrate solution. The mixture is extracted 3 times with ethyl acetate and the combined organic phases are dried over $Na_2SO_4$, filtered and concentrated. The crude product is chromatographed over 250 g of silica gel using 4:1 PE:EA.

Yield: 436 mg (50% of theory)

$R_f$=0.58 PE:EA 4:1

EXAMPLE VI

Ethyl 2-cyclopentyl-4,6-bis-(4-fluorophenyl)-3-formyl-5-carboxylate

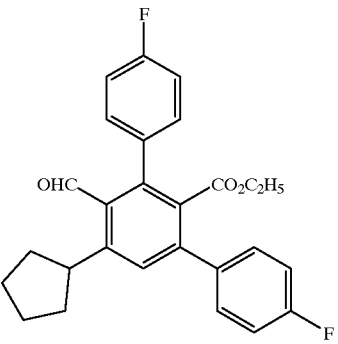

At room temperature, a mixture of 210 mg of $Al_2O_3$ and 453 mg of PCC (2 mmol) are added to a solution of 450 mg (1 mmol) of the compound from Example V in 20 ml of $CH_2Cl_2$, and the mixture is stirred for 15 h. A little silica gel is added to the suspension, which is then filtered off with suction through silica gel. The filtrate is concentrated.

Yield: 417 mg (96% of theory)

$R_f$=0.84 in PE:EA 4:1

EXAMPLE VII

Ethyl 2-cyclopentyl-4,6-bis-(4-fluorophenyl)-3-[(p-trifluoromethylphenyl)-hydroxymethyl]-phenyl-5-carboxylate

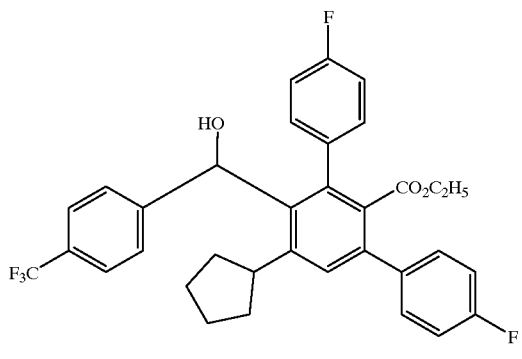

Under argon, 57.4 mg of Mg turnings are suspended in 10 ml of THF, and 566 mg (2.6 mmol) of p-trifluoromethylphenyl bromide are slowly added dropwise under reflux. After 1 h, the mixture is cooled. At −70° C., this solution is added dropwise to a solution of 400 mg (0.9 mmol) of the compound from Example VI in 10 ml of THF. The mixture is slowly warmed to 10° C. and, after 30 minutes, admixed with saturated NH$_4$Cl solution, and ethyl acetate is added. The aqueous phase is extracted once more with ethyl acetate, and the combined organic phases are dried over Na$_2$SO$_4$, filtered and concentrated. The crude product is chromatographed over 100 g of silica gel using PE:EA 6:1.

Yield: 475 mg (91% of theory)

R$_f$=0.68 in PE:EA 4:1

EXAMPLE VIII

Ethyl 2-cyclopentyl-4,6-bis-(4-fluorophenyl)-3-[(p-trifluoromethylphenyl)-fluoromethyl]-phenyl-5-carboxylate

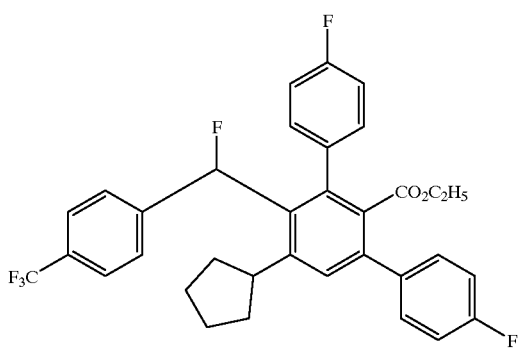

Under argon and at −30° C., 42 mg (0.26 mmol) of diethylaminosulphur trifluoride are added dropwise to a solution of 100 mg (0.17 mmol) of the compound from Example VII in 3 ml of CH$_2$Cl$_2$. After 1 h, the mixture is poured into 50 ml of saturated NaHCO$_3$ solution, and the mixture is extracted 3 times with CH$_2$Cl$_2$. The combined organic phases are dried over Na$_2$SO$_4$, filtered and concentrated. The product is dried under high vacuum.

Yield: 114 mg (115% of theory; still contains residual solvent; used as such for the next step).

R$_f$=0.81 in toluene

Preparation Examples

Example 1

2-Cyclopentyl-4,6-bis-(4-fluorophenyl)-3-[(p-trifluoromethylphenyl)-fluoromethyl-5-hydroxymethylbenzene

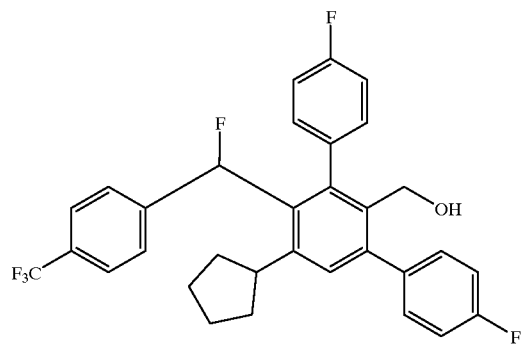

Under argon, a solution of 100 mg (0.17 mmol) of the compound from Example VIII in 2 ml of THF is added dropwise to a solution of 0.38 ml of LiAlH$_4$ (0.38 mmol) in 3 ml of THF. After 2 h at reflux, the mixture is hydrolyzed with Na,K tartrate solution and extracted 3 times with CH$_2$Cl$_2$. The combined organic phases are dried over Na$_2$SO$_4$, filtered and concentrated. The crude product is chromatographed over 20 g of silica gel using 4:1 PE:EA.

Yield: 65 mg (71% of theory)

R$_f$=0.64 PE:EA 4:1

The compounds listed in Table 1 were prepared in a similar manner:

TABLE 1

| Ex-No. | Structure | $R_f$-value/mobile phase |
|---|---|---|
| 2 | 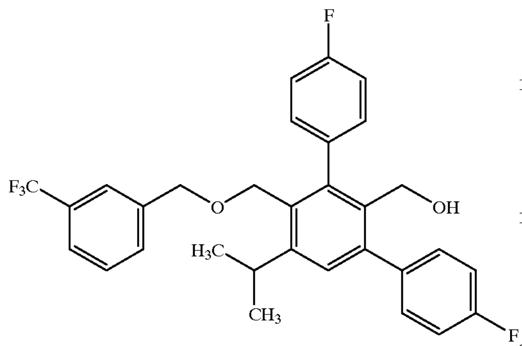 | 0.59 (PE/EA = 4:1) |
| 3 | 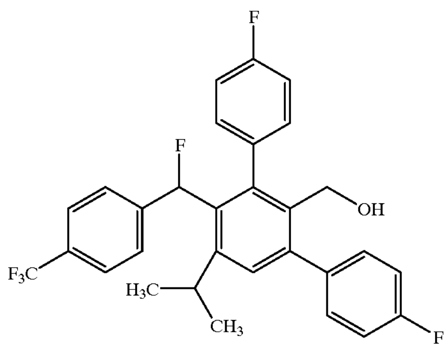 | 0.69 (PE/EA = 4:1) |
| 4 | 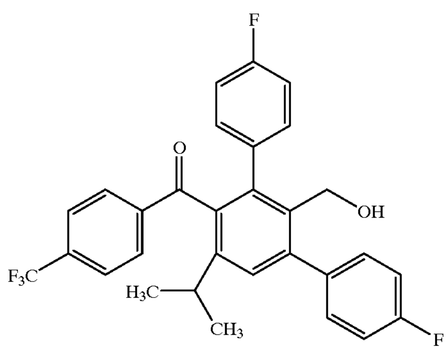 | 0.62 (PE/EA = 4:1) |
| 5 | 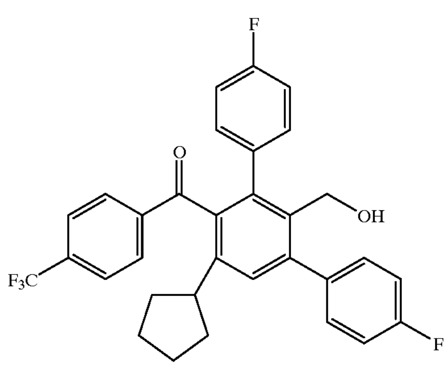 | 0.73 (PE/EA = 4:1) |

What is claimed is:

1. 5-Hydroxy-alkyl-substituted phenyls of the general formula (I)

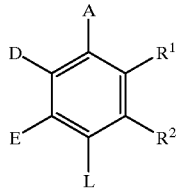
(I)

in which

A represents aryl having 6 to 10 carbon atoms which is optionally substituted up to 5 times by identical or different substituents from the group consisting of halogen, hydroxyl, trifluoromethyl, nitro, trifluoromethoxy, or by straight-chain or branched alkyl, acyl, hydroxyalkyl or alkoxy having in each case up to 7 carbon atoms, or by a group of the formula —NR$^3$R$^4$ in which $R^3$ and $R^4$ are identical or different and each represents hydrogen, phenyl, or straight-chain or branched alkyl having up to 6 carbon atoms, D represents aryl having 6 to 10 carbon atoms which is optionally substituted by nitro, halogen, trifluoromethyl or trifluoromethoxy, or represents a radical of the formula

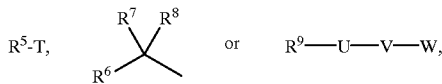

in which $R^5$, $R^6$ and $R^9$ are identical or different and each represents cycloalkyl having 3 to 6 carbon atoms or aryl having 6 to 10 carbon atoms or forms a 5- to 7-membered, optionally benzo-fused, saturated or unsaturated, mono-, bi- or tricyclic heterocycle having up to 4 carbon atoms from the group consisting of S, N and O, where the cycles, in the case of the nitrogen-containing rings also via the N-function, are optionally substituted up to 5 times by identical or different substituents from the group consisting of halogen, trifluoromethyl, nitro, hydroxyl, cyano, carboxyl, trifluoromethoxy, straight-chain or branched acyl, alkyl, alkylthio, alkylalkoxy, alkoxy and alkoxycarbonyl having in each case up to 6 carbon atoms, by aryl having 6 to 10 carbon atoms or by an optionally benzo-fused aromatic 5- to 7-membered heterocycle having up to 3 heteroatoms from the group consisting of S, N and/or O, and/or by a group of the formula —OR$^{10}$, —SR$^{11}$, —SO$_2$R$^{12}$ or —NR$^{13}$R$^{14}$, in which $R^{10}$, $R^{11}$ and $R^{12}$ are identical or different and each represents aryl having 6 to 10 carbon atoms which for its part is substituted up to 2 times by identical or different substituents from the group consisting of phenyl, halogen or by straight-chain or branched alkyl having up to 4 carbon atoms, $R^{13}$ and $R^{14}$ are identical or different and have the meaning of $R^3$ and $R^4$ given above, or $R^5$ or $R^6$ each represent a radical of the formula

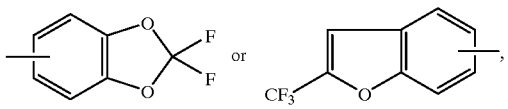

T represents straight-chain or branched alkyl or alkenyl having in each case 2 to 10 carbon atoms which are optionally substituted up to 2 times by hydroxyl, $R^7$ represents hydrogen or halogen, and $R^8$ represents hydrogen, halogen, azido, trifluoromethyl, hydroxyl, trifluoromethoxy, straight-chain or branched alkoxy having up to 5 carbon atoms or a radical of the formula —NR$^{15}$R$^{16}$, in which $R^{15}$ and $R^{16}$ are identical or different and have the meaning of $R^3$ and $R^4$ given above, or $R^7$ and $R^8$ together form a radical of the formula =O or =NR$^{17}$, in which $R^{17}$ is hydrogen or straight-chain or branched alkyl, alkoxy or acyl having in each case up to 6 carbon atoms, U and W are identical or different and each represents straight-chain or branched alkyl having up to 8 carbon atoms, or U or W represent a bond, V represents an oxygen or sulphur atom or represents a radical of the formula —NR$^{18}$, in which $R^{18}$ represents hydrogen or straight-chain or branched alkyl having up to 6 carbon atoms or phenyl, E represents cycloalkyl having 3 to 8 carbon atoms, or represents straight-chain or branched alkyl having up to 8 carbon atoms which is optionally substituted by cycloalkyl having 3 to 8 carbon atoms or hydroxyl, or represents phenyl which is optionally substituted by halogen or trifluoromethyl, L represents hydrogen, hydroxyl, straight-chain or branched alkoxy or alkyl having in each case up to 6 carbon atoms or represents a radical of the formula —NR$^{19}$R$^{20}$ or

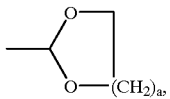

in which $R^{19}$ and $R^{20}$ have the meanings of $R^3$ and $R^4$ given above and are identical to or different from these, and a represents a number 1, 2 or 3, $R^1$ represents straight-chain or branched alkyl having up to 6 carbon atoms which is substituted by hydroxyl, $R^2$ represents aryl having 6 to 10 carbon atoms which is optionally substituted by halogen, nitro, cyano, trifluoromethyl, trifluoromethoxy, straight-chain or branched alkyl, alkoxy, acyl or alkoxycarbonyl having in each case up to 6 carbon atoms, hydroxyl, carboxyl or by a group of the formula —NR$^{21}$R$^{22}$, in which $R^{21}$ and $R^{22}$ are identical or different and have the meanings of $R^3$ and $R^4$ given above, and their salts.

2. Compounds of the general formula (I) according to claim 1, in which

A represents naphthyl or phenyl which are optionally substituted up to 3 times by identical or different substituents from the group consisting of fluorine, chlorine, bromine, amino, hydroxyl, trifluoromethyl, trifluoromethoxy, nitro, or by straight-chain or branched alkyl, or alkoxy having in each case up to 6 carbon atoms or by a group of the formula —NR$^3$R$^4$, in which R$^3$ and R$^4$ are identical or different and each represents hydrogen or straight-chain or branched alkyl having up to 4 carbon atoms, D represents phenyl which is optionally substituted by nitro, fluorine, chlorine, bromine, phenyl, trifluoromethyl or trifluoromethoxy, or represents a radical of the formula

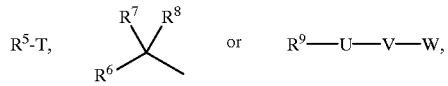

in which

R$^5$, R$^6$ and R$^9$ independently of one another each represent cyclopropyl, cyclopentyl or cyclohexyl, or phenyl, naphthyl, pyridyl, tetrazolyl, pyrimidyl, pyrazinyl, pyrrolidinyl, indolyl, morpholinyl, imidazolyl, benzothiazolyl, phenoxathiin-2-yl, benzoxazolyl, furyl, quinolyl or purin-8-yl, where the cycles are optionally substituted up to 3 times, in the case of the nitrogen-containing rings also via the N-function, by identical or different substituents from the group consisting of fluorine, chlorine, bromine, trifluoromethyl, hydroxyl, cyano, carboxyl, trifluoromethoxy, straight-chain or branched acyl, alkyl, alkylthio, alkylalkoxy, alkoxy or alkoxycarbonyl having in each case up to 4 carbon atoms, triazolyl, tetrazolyl, benzoxathiazolyl or phenyl, and/or by a group of the formula —OR$^{10}$, —SR$^{11}$ or —SO$_2$R$^{12}$, in which R$^{10}$, R$^{11}$ and R$^{12}$ are identical or different and each represents phenyl which for its part is substituted up to 2 times by identical or different substituents from the group consisting of phenyl, fluorine, chlorine or by straight-chain or branched alkyl having up to 4 carbon atoms, or R$^5$ and/or R$^6$ represent a radical of the formula

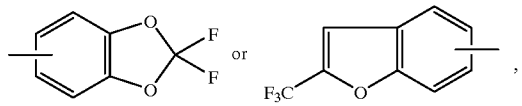

R$^7$ represents hydrogen, fluorine, chlorine or bromine, and

R$^8$ represents hydrogen, fluorine, chlorine, bromine, azido, trifluoromethyl, hydroxy, trifluoromethoxy, straight-chain or branched alkoxy or alkyl having in each case up to 5 carbon atoms or a radical of the formula —NR$^{15}$R$^{16}$, in which R$^{15}$ and R$^{16}$ are identical or different and each represents hydrogen, phenyl or straight-chain or branched alkyl having up to 4 carbon atoms, or R$^7$ and R$^8$ together form a radical of the formula =O or =NR$^{17}$, in which R$^{17}$ represents hydrogen or straight-chain or branched alkyl, alkoxy or acyl having in each case up to 4 carbon atoms, T represents straight-chain or branched alkyl or alkenyl having in each case up to 6 carbon atoms which are optionally substituted up to 2 times by hydroxyl, U and W are identical or different and each represents straight-chain or branched alkyl having up to 6 carbon atoms, or U or W represent a bond, V represents an oxygen or sulphur atom or a group of the formula —NR$^{18}$, in which R$^{18}$ represents hydrogen or straight-chain or branched alkyl having up to 4 carbon atoms or phenyl, E represents cyclopropyl, -butyl, -pentyl, -hexyl or -heptyl, or represents straight-chain or branched alkyl having up to 6 carbon atoms which is optionally substituted by cyclopropyl, -butyl, -hexyl, -pentyl, -heptyl, or by hydroxyl, or represents phenyl which is optionally substituted by fluorine, chlorine or trifluoromethyl, L represents hydrogen, hydroxyl, straight-chain or branched alkoxy or alkyl having in each case up to 5 carbon atoms or represents a radical of the formula —NR$^{19}$R$^{20}$, in which R$^{19}$ and R$^{20}$ have the meanings of R$^3$ and R$^4$ given above and are identical to or different from these, R$^1$ represents straight-chain or branched alkyl having up to 4 carbon atoms which is substituted by hydroxyl, R$^2$ represents naphthyl or phenyl which is optionally substituted by fluorine, chlorine, bromine, nitro, cyano, trifluoromethyl, trifluoromethoxy, straight-chain or branched alkyl, alkoxy, acyl or alkoxycarbonyl having in each case up to 4 carbon atoms, hydroxyl, carboxyl or by a group of the formula —NR$^{21}$R$^{22}$, in which R$^{21}$ and R$^{22}$ are identical or different and have the meanings of R$^3$ and R$^4$ given above, and their salts.

3. Compounds of the general formula (I) according to claim 1, in which

A represents phenyl which is optionally substituted up to 2 times by identical or different substituents from the group consisting of fluorine, chlorine, bromine, hydroxyl, trifluoromethyl, trifluoromethoxy, nitro, or by straight-chain or branched alkyl or alkoxy having in each case up to 5 carbon atoms or by a group of the formula —NR$^3$R$^4$, in which R$^3$ and R$^4$ are identical or different and each represents hydrogen or straight-chain or branched alkyl having up to 3 carbon atoms, D represents phenyl which is optionally substituted by nitro, phenyl, fluorine, chlorine or bromine, or represents a radical of the formula

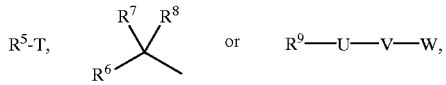

in which

R$^5$, R$^6$ and R$^9$ independently of one another each represent cyclopropyl, cyclopentyl or cyclohexyl, or phenyl, naphthyl, pyridyl, tetrazolyl, pyrimidyl, pyrazinyl, phenoxathiin-2-yl, indolyl, imidazolyl, pyrrolidinyl, morpholinyl, benzothiazolyl, benzoxazolyl, furyl, quinolyl or purin-8-yl, where the cycles are optionally substituted up to 3 times, in the case of the nitrogen-containing rings also via the N-function, by identical or different substituents from the group consisting of fluorine, chlorine, trifluoromethyl, hydroxyl, cyano, carboxyl, trifluoromethoxy, straight-chain or branched alkyl, alkylthio, alkylalkoxy, alkoxy or alkoxycarbonyl having in each case up to 3 carbon atoms, triazolyl, tetrazolyl, benzothiazolyl or phenyl, and/or by a group of the formula —$OR^{10}$, —$SR^{11}$ or —$SO_2R^{12}$, in which $R^{10}$, $R^{11}$ and $R^{12}$ are identical or different and each represents phenyl which for its part is substituted up to 2 times by identical or different substituents from the group consisting of phenyl, fluorine, chlorine, or by straight-chain or branched alkyl having up to 3 carbon atoms, or $R^5$ and/or $R^6$ represent a radical of the formula

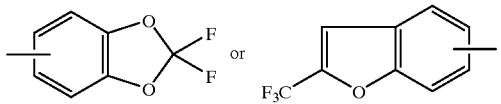

$R^7$ represents hydrogen or fluorine, and $R^8$ represents hydrogen, fluorine, chlorine, bromine, azido, trifluoromethyl, hydroxyl, trifluoromethoxy, or straight-chain or branched alkoxy or alkyl having in each case up to 4 carbon atoms or represents a radical of the formula —$NR^{15}R^{16}$, in which $R^{15}$ and $R^{16}$ are identical or different and each represents hydrogen or straight-chain or branched alkyl having up to 3 carbon atoms, or $R^7$ and $R^8$ together form a radical of the formula =O or =$NR^{17}$, in which $R^{17}$ represents hydrogen or straight-chain or branched alkyl, alkoxy or acyl having in each case up to 4 carbon atoms, T represents straight-chain or branched alkyl or alkenyl having in each case up to 4 carbon atoms which are optionally substituted up to 2 times by hydroxyl, U and W are identical or different and each represents straight-chain or branched alkyl having up to 3 carbon atoms, or U or W represent a bond, V represents an oxygen or sulphur atom or a group of the formula —$NR^{18}$, in which $R^{18}$ represents hydrogen or straight-chain or branched alkyl having up to 3 carbon atoms, E represents cyclopropyl, cyclopentyl or cyclohexyl or phenyl which is optionally substituted by fluorine or trifluoromethyl, or represents straight-chain or branched alkyl having up to 4 carbon atoms which is optionally substituted by hydroxyl, L represents hydrogen, hydroxyl, straight-chain or branched alkoxy or alkyl having in each case up to 4 carbon atoms or represents a radical of the formula —$NR^{19}R^{20}$, in which $R^{19}$ and $R^{20}$ have the meanings of $R^3$ and $R^4$ given above and are identical to or different from these, $R^1$ represents straight-chain or branched alkyl having up to 3 carbon atoms which is substituted by hydroxyl, $R^2$ represents phenyl which is optionally substituted by fluorine, chlorine, nitro, cyano, trifluoromethyl, trifluoromethoxy, straight-chain or branched alkyl, alkoxy, acyl or alkoxycarbonyl having in each case up to 3 carbon atoms, hydroxyl, carboxyl or by a group of the formula —$NR^{21}R^{22}$, in which $R^{21}$ and $R^{22}$ are identical or different and have the meanings of $R^3$ and $R^4$ given above, and their salts.

4. Process for preparing compounds of the general formula (I) according to claim 1, characterized in that

[A] in the compounds of the general formula (II)

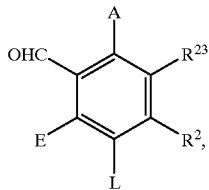

in which

A, E, L and $R^2$ are each as defined above and $R^{23}$ represents $C_1$–$C_4$-alkoxycarbonyl, initially the radical D is generated in the sense of an organometallic reaction, the substituent is optionally derivatized at this stage by customary methods and the alkoxycarbonyl group is converted into the hydroxymethyl function by reduction, or

[B] in the case that D represents the radical of the formula $R^9$—U—V—W in which V represents an oxygen atom, either compounds of the general formula (III)

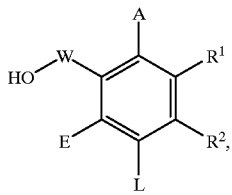

in which

A, E, L, W, $R^1$ and $R^2$ are each as defined above, are reacted with compounds of the general formula (IV)

$R^9$—U—Y          (IV), in which $R^9$ and U are each as defined above, and

Y represents halogen, preferably chlorine or bromine, in inert solvents, if appropriate in the presence of a base and/or auxiliary, or

[C] compounds of the general formula (III) are initially converted, by reaction with compounds of the general formula (V)

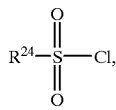

in which $R^{24}$ represents straight-chain alkyl having up to 4 carbon atoms, into the compounds of the general formula (VI)

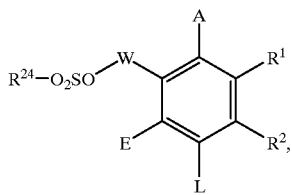 (VI)

in which

A, E, L, W, $R^1$, $R^2$ and $R^{24}$ are each as defined above, and these are subsequently reacted with compounds of the general formula (VII)

$R^9$—U—V—H    (VII), in which $R^9$, U and V are each as defined above, and protective groups are, if appropriate, removed, and the substituents listed under D, E, L and/or $R^1$ and $R^2$ are, if appropriate, varied or introduced by customary methods.

5. A pharmaceutical composition comprising at least one 5-hydroxy-alkyl-substituted phenyl according to claim 1 and a pharmacologically acceptable auxiliary.

6. A method of treating arteriosclerosis in a patient comprising administering to such patient an effective amount therefor of a 5-hydroxy-alkyl-substituted phenyl according to claim 1.

7. A method of treating hyperlipoproteinaemia in a patient comprising administering to such patient an effective amount therefor of a 5-hydroxy-alkyl-substituted phenyl according to claim 1.

* * * * *